United States Patent [19]

Pogue et al.

[11] Patent Number: 5,430,211
[45] Date of Patent: Jul. 4, 1995

[54] PROCESS OF PREPARING ETHYLBENZENE OR SUBSTITUTED DERIVATIVES THEREOF

[75] Inventors: Randall F. Pogue, Friendswood, Tex.; Juan M. Garces, Midland, Mich.; Timothy M. May, Lake Jackson, Tex.; Andrew Q. Campbell, Midland, Mich.

[73] Assignee: The Dow Chemical Company, Midland, Mich.

[21] Appl. No.: 146,355

[22] Filed: Oct. 29, 1993

[51] Int. Cl.$^6$ .............................................. C07C 2/66
[52] U.S. Cl. .................................. 585/323; 585/467; 585/654
[58] Field of Search ............... 585/323, 446, 467, 654, 585/658, 650

[56] References Cited

U.S. PATENT DOCUMENTS

| | | | |
|---|---|---|---|
| 3,247,278 | 4/1966 | Garwood et al. | 260/683.3 |
| 3,383,431 | 5/1968 | Fishel | 260/683.3 |
| 3,494,970 | 2/1970 | Pharis | 260/671 |
| 3,502,739 | 3/1970 | Begley et al. | 260/680 |
| 3,538,176 | 11/1970 | Bloch | 260/671 |
| 3,576,766 | 4/1971 | Ransch | 252/439 |
| 3,700,749 | 10/1972 | Robinson | 260/683.3 |
| 3,751,604 | 8/1973 | Keown et al. | 260/672 |
| 3,756,942 | 9/1973 | Cattanach | 208/137 |
| 4,085,156 | 4/1978 | Frilette et al. | 260/671 |
| 4,086,287 | 4/1978 | Kaeding et al. | 260/671 |
| 4,107,224 | 8/1978 | Dwyer | 260/671 |
| 4,117,024 | 9/1978 | Kaeding | 260/671 R |
| 4,175,057 | 11/1979 | Davies et al. | 252/455 |
| 4,259,537 | 3/1981 | Chu | 585/467 |
| 4,350,835 | 9/1982 | Chester et al. | 585/467 |
| 4,499,320 | 2/1985 | Garces | 585/467 |
| 4,523,048 | 6/1985 | Vora | 585/323 |
| 4,524,230 | 6/1985 | Haensel | 585/467 |
| 4,585,641 | 4/1986 | Barri et al. | 423/331 |
| 4,654,316 | 3/1987 | Barri et al. | 502/61 |
| 4,654,454 | 3/1987 | Barri et al. | 585/415 |
| 4,670,614 | 6/1987 | Ushio et al. | 585/417 |
| 4,788,364 | 11/1988 | Harandi | 585/312 |
| 4,879,424 | 11/1989 | Harandi | 585/322 |
| 4,891,458 | 1/1990 | Innes et al. | 585/323 |
| 5,012,021 | 4/1991 | Vora et al. | 585/315 |
| 5,081,323 | 1/1992 | Innes et al. | 585/449 |
| 5,138,113 | 8/1992 | Juguin et al. | 585/322 |
| 5,145,817 | 9/1992 | Sherrod | 502/65 |
| 5,175,135 | 12/1992 | Lee et al. | 502/64 |

OTHER PUBLICATIONS

Derwent Abstract No. 35,033Q (1966).

*Primary Examiner*—P. Achutamurthy
*Attorney, Agent, or Firm*—Marie F. Zuckerman

[57] ABSTRACT

A process of preparing ethylbenzene from ethane and benzene as raw materials. The process involves (1) contacting ethane in a dehydrogenation zone with a dehydrogenation catalyst, namely, a mordenite zeolite, optionally, containing a metallic component selected from gallium, zinc, and the platinum group metals under reaction conditions which yield a dilute ethylene stream in ethane. Thereafter, the ethylene stream with essentially no further purification or separation is contacted in an alkylation zone with benzene in the presence of an alkylation catalyst, such as an acidic zeolite or a porous magnesium silicate, under reaction conditions such that ethylbenzene is formed.

20 Claims, No Drawings

5,430,211

PROCESS OF PREPARING ETHYLBENZENE OR SUBSTITUTED DERIVATIVES THEREOF

BACKGROUND OF THE INVENTION

This invention relates to a process of preparing ethylbenzene or substituted derivatives thereof using ethane and benzene, or ethane and substituted benzenes, as raw materials.

Ethylbenzene and substituted ethylbenzenes are useful for preparing styrene and substituted styrenes, which are starting materials for polystyrene plastics.

Ethylbenzene is almost exclusively prepared by the alkylation of benzene with ethylene. Commercial processes include liquid phase alkylation with Friedel-Crafts catalysts, such as aluminum chloride and phosphoric acid, as well as, vapor phase alkylation with acidic carrier catalysts, such as crystalline alumino-silicates. Disadvantageously, these commercial processes require an essentially pure stream of ethylene.

Ethylene is obtained predominantly from the thermal cracking of saturated hydrocarbons, such as natural gas rich in ethane, propane and n- and iso-butane. Alternatively, ethylene can be obtained from the thermal or steam cracking of naphtha. Disadvantageously, crackers also produce a variety of other products, including diolefins and acetylene, which are costly to separate from ethylene. Separation methods include extractive distillation and/or selective hydrogenation of the acetylene back to ethylene. Cracking and separation technologies for the obtention of pure ethylene account for approximately one-third of the total ethylbenzene production costs.

U.S. Pat. No. 5,138,113, for example, teaches a two-step cracking-alkylation process for producing alkylaromatic hydrocarbons from natural gas, the process comprising: 1) thermal cracking of the natural gas with formation of hydrogen and $C_{2-3}$ hydrocarbons, particularly, ethylene and acetylene, 2) separation of the $C_{2-3}$ hydrocarbons particularly of the ethylene and the acetylene obtained at the end of stage (1) by cooled adsorption in a solvent, and 3) conversion of the $C_{2-3}$ hydrocarbons from stage (2) into alkylaromatics. As noted hereinbefore, this type of process is hampered by its dependency on a conventional thermal cracker and cryogenic separation of ethylene from acetylene.

U.S. Pat. No. 4,524,230 discloses an alternative method for preparing alkylaromatic compounds comprising a one-step cracking-alkylation process utilizing a paraffinic hydrocarbon as a source of an alkylating agent. The reaction comprises cracking a paraffinic hydrocarbon into olefinic products on the surface of a non-acid catalyst in the presence of an aromatic compound. The non-acid catalyst comprises a metal from Group VIII of the Periodic Table and may be supported on an alkylation catalyst, preferably, an aluminosilicate zeolite. The olefinic products produced in situ act as alkylating agents towards the aromatic compounds to produce alkylaromatic compounds. Disadvantageously, the selectivity to monoalkylated aromatics is low and unwanted polyalkylated benzenes are produced in large amounts. Moreover, the cracking of the paraffinic hydrocarbon in situ leads to impurities, such as acetylene and diolefins, which reduce the lifetime of the alkylation catalyst.

One method of reducing ethylene costs is to alkylate with dilute ethylene streams, which are available from most refinery FCC units. U.S. Pat. No. 4,107,224 discloses the vapor phase alkylation of benzene to ethylbenzene using a ZSM-5 zeolite as the catalyst. It is taught that the catalyst can handle feedstreams containing from about 15 to about 20 weight percent ethylene while yielding an ethylbenzene purity of greater than 97 weight percent. Disadvantageously, the procurement of the dilute ethylene stream is dependent upon a refinery by-product stream. More disadvantageously, the dilute ethylene stream may contain impurities, such as diolefins and acetylene, which reduce the lifetime of the alkylation catalyst, unless the impure streams are purified first.

In view of the above, it would be desirable to have a process of preparing ethylbenzene or substituted ethylbenzenes which does not rely on conventional thermal crackers and expensive separation technologies for a source of essentially pure ethylene. It would be even more desirable if the process could employ a dilute source of ethylene which is not dependent upon refinery streams and which is not contaminated with impurities which lower the lifetime of the alkylation catalyst.

SUMMARY OF THE INVENTION

This invention comprises a two-step process of preparing ethylbenzene or substituted ethylbenzenes. The process of this invention uses, as raw materials, ethane and benzene or substituted benzene. The process comprises dehydrogenating ethane to produce a dilute stream of ethylene, and thereafter, alkylating benzene or substituted benzene with the dilute ethylene stream to yield ethylbenzene or substituted ethylbenzene.

The dehydrogenation step comprises contacting an ethane feedstream with a catalytic amount of a dehydrogenation catalyst in a dehydrogenation zone. The contacting is conducted under reaction conditions such that a dehydrogenation product stream containing predominantly ethylene and unreacted ethane is formed. The dehydrogenation catalyst comprises a mordenite zeolite and, optionally, a metal component selected from the group consisting of gallium, zinc, and the platinum group metals of the Periodic Table. Thereafter, in the second step the dehydrogenation product stream, with essentially no further purification or separation, and a benzene co-feed are contacted with a catalytic amount of an alkylation catalyst in an alkylation zone under reaction conditions such that ethylbenzene is produced. Alternatively, a substituted benzene may be employed in the alkylation zone to produce a substituted ethylbenzene product.

The process of this invention advantageously does not require a thermal cracker or expensive separation technologies. Moreover, the dehydrogenation step in the process of this invention produces ethylene in high selectivity without the formation of unwanted impurities, such as acetylene and diolefins. Consequently, the dehydrogenation product stream which contains predominantly unreacted ethane and a dilute concentration of ethylene can be fed without further purification or separation directly to the alkylation zone. As an added advantage, the alkylation product stream is easily separated via fractional distillation. Unreacted ethane can be recycled to the dehydrogenation zone. Unreacted benzene or substituted benzene can be recycled to the alkylation zone. Diethyl or triethylbenzenes, if they are produced, can be directed to a transalkylation reactor, and the ethylbenzene product is recovered for use. Most advantageously, the alkylation product stream contains high yields of ethylbenzene or substituted ethylbenzenes.

DETAILED DESCRIPTION OF THE INVENTION

In the process of this invention a two-stage reactor system is employed to produce ethylbenzene or a substituted derivative thereof from ethane and benzene or substituted benzene.

In a preferred embodiment of this invention, ethane and benzene are converted in a two-stage process to ethylbenzene. In the first stage, ethane is contacted in a dehydrogenation zone with a mordenite zeolite catalyst, optionally, containing gallium, zinc, or a platinum group metal, preferably platinum or ruthenium, to produce a dehydrogenation stream containing predominantly unreacted ethane and dilute quantities of ethylene. The dilute ethylene stream is fed with essentially no further separation or purification into an alkylation zone. There, the dilute ethylene stream is contacted with benzene in the presence of an alkylation catalyst under reaction conditions such that ethylbenzene is produced. The alkylation catalyst is selected from a variety of alkylation catalysts including magnesium silicates and zeolites, such as, mordenite, ZSM-5, zeolite beta, and zeolite Y, the zeolites being used in their acid form.

Ethane is required for the process of this invention. Any source of ethane is acceptable, as for example, ethane derived from natural gas or naphtha. Typically, the ethane is essentially free of benzene or substituted benzenes. The term "essentially free" means that the amount of benzene or substituted benzenes is less than about 1 weight percent, typically, less than about 0.1 weight percent. Optionally, the ethane feed can be diluted with an inert diluent, such as nitrogen, helium, or steam. The concentration of ethane in the feedstream typically ranges from about 10 to about 100 volume percent.

The ethane dehydrogenation catalyst comprises a mordenite zeolite and, optionally, a metal component selected from the group consisting of gallium, zinc, and the platinum group metals of the Periodic Table. The structure and properties of mordenite zeolite are described in Zeolite Molecular Sieves, by Donald W. Breck (John Wiley & Sons, 1974), at pages 122–124 and 162–163, which is incorporated herein by reference. Mordenites useful for the dehydrogenation process of this invention possess a silica to alumina molar ratio ranging between about 10 and about 500, preferably, between about 10 and about 100.

Any mordenite dehydrogenation catalyst having the above-identified silica to alumina molar ratio can be employed in the dehydrogenation step. Suitable mordenites are available commercially or may be prepared by dealumination techniques known to those skilled in the art. In a preferred embodiment, the mordenite is acid treated and acid extracted as described in U.S. Pat. No. 4,891,448, the relevant sections of which are incorporated herein by reference. In an alternative preferred embodiment, sodium or acid mordenite is impregnated or ion-exchanged with one or more of gallium, zinc, and the platinum group metal ions (Rh, Pd, Pt, Ru, Os, Ir). More preferably, the starting mordenite is impregnated or ion-exchanged with gallium, zinc, platinum or ruthenium, or combinations thereof. Most preferably, the starting mordenite is impregnated or ion-exchanged with gallium.

Impregnation and ion-exchange procedures are also well known in the art. For example, suitable metal ion exchanged or impregnated mordenites are described in U.S. Pat. Nos. 4,670,614, and 4,654,316, relevant sections of which are incorporated herein by reference. Typically, impregnation comprises depositing a solution containing soluble salts of the metal ions of interest, such as the metal nitrates, on the mordenite zeolite to the point of incipient wetness. Alternatively, ion-exchange comprises slurrying the sodium or acid mordenite at a temperature between ambient and about 100° C. with a solution containing soluble salts of the metals of interest until such time as the sodium or hydrogen ions of the mordenite are partially or fully exchanged with the desired metal ions. Solution molarities generally range from about 1M to about 6M, and the volume of solution per gram of mordenite generally ranges from about 5 ml/g to about 20 ml/g. The impregnated or exchanged mordenite is thereafter calcined under air at a temperature between about 300° C. and about 700° C., preferably between about 450° C. and about 550° C. Generally, the metal loading ranges from about 0.1 to about 20 weight percent.

While the dehydrogenation step can be conducted in any reactor including batch reactors, fixed-bed reactors, fluidized bed reactors, and transport reactors, it is preferred that the reactor be a fixed-bed, continuous flow design.

Any operable process conditions are suitable for the dehydrogenation step of this invention provided that ethylene is produced in high selectivity. It is typical for the operating temperature to range between about 400° C. and about 900° C., and preferably, between about 550° C. and about 750° C. Below the lowest temperature, the conversion of ethane may be too low. Above the highest temperature, selectivities to unwanted cracking products may increase. It is possible to conduct the dehydrogenation process at subatmospheric or superatmospheric pressures. Preferably, the process is conducted at a pressure between subatmospheric and about atmospheric, preferably, between about 1 psig and about 1 atmosphere.

In a fixed-bed continuous flow reactor the residence time of the ethane feedstream and the relative amount of ethane to catalyst is given by the gas hourly space velocity. For the purposes of this invention, the gas hourly space velocity (GHSV) is defined as the volume of gaseous feedstream per reactor volume per hour, or simply, $hr^{-1}$. Generally, the GHSV ranges from about 100 $hr^{-1}$ to about 5,000 $hr^{-1}$. Preferably, the GHSV ranges from about 500 $hr^{-1}$ to about 1,500 $hr^{-1}$. Below the lowest typical GHSV, the selectivity to ethylene may decrease and the selectivity to aromatics may increase. Above the highest typical GHSV, the conversion of ethane may be too low. When the GHSV is maintained within the broad range specified hereinabove, the selectivity to ethylene is high and by-product formation is very low.

When the dehydrogenation process is conducted under the reaction conditions specified hereinabove, the product stream comprises predominantly ethylene and unreacted ethane. For the purposes of this invention, the term "conversion of ethane" refers to the weight percentage of ethane which is converted into products. Typically, the conversion of ethane is greater than about 5 weight percent, preferably, greater than about 14 weight percent, more preferably, greater than about 35 weight percent, and most preferably, greater than about 45 weight percent. Also, for the purposes of this invention the term "selectivity" refers to the weight percentage of converted ethane which forms a particular product. For example, the selectivity to ethylene is typically greater than about 70 weight percent, more preferably, greater than about 80 weight percent, and most preferably, greater than about 85 weight percent. In typical embodiments a dilute ethylene stream is obtained comprising ethylene in a concentration ranging from about 5 to about 50 weight percent, preferably, from about 10 to about 43 weight percent.

Advantageously, the selectivities to aromatic products, such as benzene, toluene, xylenes, and C9+ compounds, are low, as are the selectivities to other aliphatic hydrocarbons, such as methane, propane, and propylene. In small amounts all of the aforementioned by-products are tolerated very well by the alkylation catalyst. Accordingly, the dilute ethylene stream can be fed, with essentially no further purification or separation, into an alkylation reactor for the alkylation of benzene or substituted benzene.

Any monocyclic aromatic compound may be monoalkylated by the process of this invention. The aromatic compound is preferably benzene or substituted benzene. Typical substituents include hydroxy, amino, halo, and $C_{1-10}$ alkyl moieties. Non-limiting examples of substituted benzenes which may be monoalkylated by the process of this invention include toluene, xylene, phenol, and aniline. More preferably, the aromatic compound is benzene.

For a liquid phase process the aromatic compound may be used neat in a liquid state, or dissolved in a suitable solvent. Preferably, the aromatic compound is used in a neat liquid state. If a solvent is employed, any inert solvent which solubilizes the aromatic compound and does not hinder the monoalkylation reaction may be used. The preferred solvent is a saturated hydrocarbon. Alternatively, the aromatic compound may be used as a vapor, optionally diluted with a gas which is non-reactive in the process of the invention, such as nitrogen, helium, or argon.

The alkylation catalyst can be selected from among any alkylation catalysts. Preferably, the alkylation catalyst is selected from the group consisting of porous crystalline magnesium silicate compositions and aluminosilicate zeolites, including mordenite, beta, ZSM-5 and Y. The intended porous crystalline magnesium silicate compositions correspond to the following formula in terms of the molar ratios of oxides on a dry basis:ps

wherein M is at least one ion-exchangeable cation having a valence of n; R is at least one element with valence +3 which is not ion-exchangeable by conventional means, such as aluminum, iron, chromium, boron, and gallium; x/z is greater than 0; y/z is greater than or equal to 0; p/n is greater than y; p, x, and z, are positive numbers; and y is a positive number or zero. A detailed description of the porous crystalline magnesium silicates, their method of preparation, and their use in the alkylation of aromatic compounds can be found in U.S. Pat. No. 4,499,320, incorporated herein by reference.

The mordenite zeolite which is useful in the alkylation step of this invention may be any acid mordenite known for such a purpose. Preferably, the acid mordenite which is employed has a silica/alumina molar ratio of at least 30:1. More preferably, the acid mordenite has a silica/alumina molar ratio of at least about 160:1, more preferably at least about 175:1, even more preferably at least about 190:1. Generally the silica/alumina molar ratio of the acid-treated mordenite catalyst is not higher than about 2500:1, more preferably not higher than about 1000:1.

In addition, the preferred mordenite possesses an X-ray diffraction pattern and porosity essentially identical to the mordenite described in U.S. Pat. No. 5,175,135, incorporated herein by reference. That mordenite catalyst has a Symmetry Index (SI) as defined hereinafter of at least about 1.0. Preferably, the Symmetry Index ranges from about 1 to about 2. The Symmetry Index is a dimensionless number obtained from the X-ray diffraction pattern of the mordenite. Mordenite zeolites exhibit an X-ray diffraction pattern whose diffraction peaks have d-spacings corresponding to those of crystalline mordenites as reported by J. D. Sherman and J. M. Bennett in "Framework Structures Related to the Zeolite Mordenite," Molecular Sieves; J.W. Meier and J.B. Uytterhoeven, eds., Advances in Chemistry Series, 121, 1973, pp. 52–65. The Symmetry Index is defined as the sum of the peak heights of the [111] (13.45, 2θ) and [241] (23.17 2θ) reflections divided by the peak height of the [350] (26.25 2θ) reflection. The porosity of the preferred mordenite is such that the total pore volume is in the range from about 0.18 cc/g to about 0.45 cc/g, and the ratio of the combined meso- and macropore volume to the total pore volume is in the range from about 0.25 to about 0.75. For the purposes of this invention, a micropore has a radius in the range of about 3 angstrom units (Å) to 10 Å, a mesopore has a radius in the range of 10 Å to 100 Å, and a macropore has a radius in the range of 100 Å to 1000 Å.

The preferred mordenite catalyst is prepared by a process which comprises treating an acidic mordenite zeolite having a silica/alumina molar ratio less than 30:1 and a Symmetry Index (SI) of from about 0.5 to about 1.3 with a strong acid, calcining the acid treated mordenite, and retreating the calcined mordenite with strong acid under conditions sufficient to provide a catalyst having a silica/alumina molar ratio equal to or greater than 30/1. Details of the preparation of the preferred acid mordenite and its use in the alkylation of aromatic compounds are set forth in U.S. Pat. Nos. 5,175,135 and 5,243,116, incorporated herein by reference.

Any acidic ZSM-5, beta and Y zeolites can be employed as catalysts in the alkylation step of this invention. Preferred are the acid ZSM-5 zeolites described in U.S. Pat. Nos. 3,751,504 and 3,756,942, incorporated herein by reference, as well as ZSM-5 zeolites modified with phosphate or Group VIA metals such as those described in U.S. Pat. Nos. 4,259,537 and 4,086,287, all citations being incorporated herein by reference.

Any acid beta zeolite can be employed in the alkylation process of this invention, but preferably, the beta zeolite is as described in U.S. Pat. Nos. 4,891,458 and 5,081,323, incorporated herein by reference. Likewise, any acid Y zeolite can be employed in the alkylation process of this invention, but preferably the Y zeolite is as described in U.S. Pat. No. 5,145,817, incorporated herein by reference.

The ratio of benzene or substituted benzene to alkylation catalyst may be any weight ratio which produces the desired monoalkylated benzene with a relatively high selectivity, the dialkylated benzene being the major by-product with low levels of tri-, tetra-, or higher polyalkylated products and a low level of other impurities. Preferred ratios will also be dependent on the way the process is operated. In a continuous mode of operation the weight hourly space velocity (WHSV) of the overall feed with respect to catalyst is preferably in the range from about 0.1 to 100 hr$^{-1}$. More preferably, the WHSV is in the range from about 0.5 to 20 hr$^{-1}$.

In the alkylation step the molar ratio of benzene or substituted benzene to ethylene may vary depending on the substituents on the benzene, type of reaction such as batch or continuous, and reaction conditions such as temperature, pressure and weight or gas hourly space velocity. In a continuous alkylation process, the ratio of benzene or substituted benzene to ethylene is preferably at least 1:1, more preferably between about 1:1 and 20:1, and even more preferably between from about 2:1 to 5:1.

The contacting of the benzene or substituted 5 benzene with ethylene in the presence of the catalyst may occur in a reactor of any configuration. Batch-type and continuous reactors, such as fixed bed, slurry bed, fluidized bed, catalytic distillation, or countercurrent reactors, are suitable configurations for the contact. Preferably, the reactor is a continuous flow reactor.

The alkylation stage of this process invention which employs an acidic mordenite zeolite as the alkylation catalyst can be carried out under conditions sufficient to keep the reaction mixture in the liquid phase. This means that substantially no gaseous zone is present in the reactor. With substantially no gaseous zone is meant that the gaseous zone comprises at the most 5 percent by volume of the reaction zone, preferably, at the most 1 percent by volume. Most preferably, the reactor is operated in a full liquid mode.

The benzene or substituted benzene may be in the molten, liquid form or in solution. Ethylene may be introduced in the liquid or gaseous state, and should substantially dissolve in the liquid phase. The catalyst may be used in various forms, such as a fixed bed, moving bed, or fluidized bed. In the liquid phase alkylation process, the contacting of the reactants in the presence of the catalyst may occur at any temperature and pressure conditions sufficient to keep the reaction mixture in the liquid phase. Typically, the temperature is in the range from about 100° C. to about 300° C. These temperatures are relatively mild for zeolite catalyzed type alkylation processes. Below the lower limit of 100° C. the reaction proceeds slowly. In a 5 preferred mode the temperature is in the range from about 170° C. to about 280° C.

Alternatively, the alkylation stage can be carried out under conditions sufficient to keep the reactants in the vapor phase. Typically, the temperature is in the range from about 200° C. to about 800° C., preferably, in the range from about 250° C. to about 600° C. Preferably, the pressure falls between atmospheric and about 35 atm.

Following the alkylation of the benzene or substituted benzene, the product mixture may be separated by standard techniques, such as distillation. Unreacted ethane, which is part of the ethylene feedstream, can be recycled back to the dehydrogenation reactor. Unreacted benzene or substituted benzene may be recycled to the alkylation reactor. As a third fraction in the distillation sequence, substantially pure monoethylated benzene or monoethylated substituted benzene is recovered. The substituted moieties are those disclosed hereinbefore with regard to the substituted benzene reagent. A fourth fraction from the distillation may be obtained containing polyethylated benzene or polyethylated substituted benzene products and heavies, such as diethylated products and optionally tri- and/or tetraethylated products. If necessary, this latter fraction, typically containing no tetraethylated products, may be fed to a subsequent transalkylation process. If desired, it is also possible to recycle ethylbenzene or substituted ethylbenzene to the alkylation reactor for further alkylation to diethylbenzene or substituted diethylbenzene.

For the purposes of this invention, the ethylene conversion is taken as the weight percentage of ethylene converted to products. Typically, the ethylene conversion is greater than about 20 weight percent, preferably, greater than about 40 weight percent, more preferably, greater than about 60 percent, and most preferably, greater than about 90 percent. The alkylation selectivity to a particular product is defined as the weight percentage of converted ethylene which forms that product, such as ethylbenzene. These selectivities are best calculated on the basis of the aromatic products formed; therefore, the amounts of unreacted ethane and benzene, as well as, the amounts of hydrogen and light hydrocarbons (e.g., methane, propane, propylene) present in the ethylene feedstream are subtracted out of the product distribution. On this basis, the selectivity to ethylbenzene or substituted ethylbenzene is typically greater than about 50 weight percent, preferably, greater than about 70 weight percent, and more preferably, greater than about 85 weight percent.

The following examples are given to illustrate the process and claims of the invention, but these examples should not be construed to be limiting thereof.

Preparation of a Dehydrogenation Catalyst Comprising Dealuminated Mordenite (SiO$_2$//Al$_2$O$_3$=23.8) Exchanged with Gallium A dry aliquot (30 g) of dry acid mordenite having a SiO$_2$/Al$_2$O$_3$ molar ratio of 23.8 is mixed with a solution comprising gallium nitrate dissolved in 15 ml of water. The amount of gallium nitrate used is such that the Ga/Al atomic ratio in the mixture is 1/1. The resulting paste is blended until homogeneous and then calcined at 500° C. in air overnight to yield a gallium-exchanged mordenite having the following properties: gallium loading, 18.2 percent, SiO$_2$/Al$_2$O$_3$ molar ratio, 23.8.

Preparation of an Alkylation Catalyst Comprising Dealuminated Acid Mordenite

An alkylation catalyst is prepared by slurrying a commercially available sodium mordenite (300 g) having a SiO$_2$/Al$_2$O$_3$ molar ratio of 19 and a Symmetry Index of 1.26 with 3000 ml of a 1M hydrochloric acid solution for 30 minutes at room temperature. The acidified product is washed with three 2000 ml portions of water and calcined overnight at 700° C. The calcined solid is stirred in 1500 ml of 6M hydrochloric acid and heated under reflux for two hours. The product is washed with two 2000 ml portions of water. The calcination and hydrochloric acid treatment are repeated a second time. product is then washed with two 2000 ml portions of water and dried at 150° C. in air overnight to yield an acidic mordenite catalyst having the following properties: SiO$_2$/Al$_2$O$_3$ molar ratio, 196; Symmetry Index, 1.98. The acidic mordenite is pelletized with 20 percent silica binder.

Example 1

The reactor consists of two microreactors connected in series. Each microreactor consists of a quartz tube (16 cm × 10 mm i.d.) which tapers to a capillary outlet. The microreactor tubes are heated with Lindberg ceramic furnaces, which are surrounded by ¾" insulation and enclosed within a stainless steel shell. The controller sensor is a type K thermocouple located inside each catalyst bed.

The first microreactor is loaded with about 1.25 cc of the gallium-exchanged mordenite dehydrogenation catalyst, prepared hereinabove, and is operated at 700° C. and a GHSV of 1200 hr$^{-1}$ for the dehydrogenation of ethane to ethylene. The outlet stream from the first microreactor is fed directly to the inlet of the second microreactor. The second microreactor is loaded with about 1.25 cc of the alkylation catalyst comprising the dealuminated acidic mordenite prepared hereinabove. The second microreactor outlet stream is sent directly to a gas chromatograph for analysis.

Each furnace is heated to its respective reaction temperature under a flow of nitrogen. Once the microreactors reach their respective reaction temperatures, they are allowed to equilibrate for approximately 15 minutes each. Ethane is then introduced to the first microreactor and a product analysis is performed to verify the ethane conversion and selectivity to ethylene, as seen in Table I. It is seen that gallium-exchanged mordenite is capable of dehydrogenating ethane in a conversion of 14 weight percent to ethylene in a selectivity of about 85 weight percent.

TABLE I

Dehydrogenation of Ethane Over Mordenite Catalysts

| Example | 1 | 2 | 3 | 4 |
|---|---|---|---|---|
| Catalyst | Ga-Mor | Zn-Mor | Ru-Mor | Mor |
| SiO$_2$/Al$_2$O$_3$ | 23.8 | 19 | 19 | 112 |
| T (°C.) | 700 | 700 | 700 | 700 |
| P (atm) | 1 | 1 | 1 | 1 |
| GHSV (hr$^{-1}$) | 1200 | 1200 | 1100 | 1200 |
| Ethane Conversion (Wt. %) | 14 | 50 | 48 | 14 |
| Equilibrium Selectivities (Wt. %): | | | | |
| Methane | 5.9 | 9.2 | 9.0 | 6.8 |
| Ethylene | 85.6 | 85.2 | 86.1 | 85.6 |
| Propane | 0.0 | 0.3 | 0.2 | 0.0 |
| Propylene | 0.0 | 2.6 | 1.8 | 0.0 |
| C4's | 1.0 | 0.4 | 0.3 | 0.8 |
| Hydrogen | 7.0 | NM① | NM① | 6.4 |
| Benzene | 0.4 | 1.4 | 1.5 | 0.4 |
| Toluene | 0.0 | 0.6 | 0.6 | 0.0 |
| Xylenes | 0.0 | 0.2 | 0.4 | 0.0 |
| C9+'s | 0.0 | 0.0 | 0.0 | 0.0 |
| Total Aromatics | 0.4 | 2.2 | 2.5 | 0.4 |

①NM = not measured.

The ethylene stream, about 12 weight percent in concentration, and a benzene co-feed are thereafter added directly to the inlet of the second microreactor. Alkylation process conditions and product distributions are set forth in Table II.

TABLE II①

Alkylation of Benzene by a Dilute Ethylene Stream Over Acid Mordenite (SiO$_2$/Al$_2$O$_3$ = 196)

| Run | A | B | C | D | E |
|---|---|---|---|---|---|
| Temp °C. | 270 | 350 | 450 | 550 | 450 |
| Pressure (atm) | 1 | 1 | 1 | 1 | 1 |
| Benzene, LHSV (hr$^{-1}$) | 3.0 | 3.0 | 3.0 | 3.0 | 3.5 |
| Ethane GHSV② (hr$^{-1}$) | 1200 | 1200 | 1200 | 1200 | 1000 |
| Ethylene Conv (wt. %) | 23 | 32 | 43 | 22 | 94 |
| Selectivities: (wt. %) | | | | | |
| Methane | 0.5 | 0.6 | 0.6 | 0.7 | 0.5 |
| Ethane | 26.9 | 32.9 | 34.5 | 34.3 | 20.8 |
| Ethylene | 4.3 | 4.2 | 3.1 | 4.9 | 0.3 |
| Propane | 0.0 | 0.0 | 0.0 | 0.0 | 0.0 |
| Propylene | 0.0 | 0.0 | 0.0 | 0.0 | 0.0 |
| Hydrogen | 0.6 | 0.8 | 0.8 | 0.9 | 0.4 |
| Benzene | 63.3 | 54.6 | 51.9 | 55.5 | 65.2 |
| Toluene | 0.0 | 0.0 | 0.9 | 0.6 | 0.9 |
| p-xylenes | 0.0 | 0.0 | 0.0 | 0.0 | 0.1 |
| m-Xylene | 0.0 | 0.0 | 0.0 | 0.0 | 0.2 |
| o-Xylene | 0.2 | 0.1 | 0.0 | 0.0 | 0.1 |
| Ethylbenzene | 3.7 | 6.2 | 7.5 | 2.9 | 10.1 |
| Styrene | 0.0 | 0.0 | 0.3 | 0.1 | 0.6 |
| C9's | 0.0 | 0.0 | 0.0 | 0.0 | 0.0 |
| Polyethylbenzenes | 0.5 | 0.5 | 0.4 | 0.0 | 0.7 |

①Alkylating feedstream, 12 wt % ethylene, no C3+ compounds.
②Ethane GHSV, as delivered to the dehydrogenation reactor.

The data in Table II are recalculated based on the total amount of alkylated aromatic compounds produced, by subtracting out the ethane and benzene feedstreams, hydrogen, and light hydrocarbons products, such as methane and ethylene. Recalculated values are found in Table III.

TABLE III①·②

Alkylation of Benzene with a Dilute Ethylene Stream over Acid Mordenite (SiO$_2$/Al$_2$O$_3$ = 196)

| Run: | A | B | C | D | E |
|---|---|---|---|---|---|
| Temp (°C.) | 270 | 350 | 450 | 550 | 450 |
| Pressure (atm) | 1 | 1 | 1 | 1 | 1 |
| Benzene LHSV (hr$^{-1}$) | 3.0 | 3.0 | 3.0 | 3.0 | 3.5 |
| Ethane GHSV③ (hr$^{-1}$) | 1200 | 1200 | 1200 | 1200 | 1000 |
| Ethylene Conv (wt %) | 23 | 32 | 43 | 22 | 94 |
| Selectivities: (wt %) | | | | | |
| Toluene | 0.0 | 0.0 | 9.9 | 16.7 | 6.9 |
| p-Xylene | 0.0 | 0.0 | 0.0 | 0.0 | 1.0 |
| m-Xylene | 0.0 | 0.0 | 0.0 | 0.0 | 1.8 |
| o-Xylene | 4.5 | 1.5 | 0.0 | 0.0 | 0.8 |
| Ethylbenzene (EB) | 84.1 | 91.0 | 82.4 | 80.6 | 79.1 |
| Styrene | 0.0 | 0.0 | 3.3 | 2.8 | 5.0 |
| C9's | 0.0 | 0.0 | 0.0 | 0.0 | 0.0 |
| C10+ Poly's | 11.4 | 7.3 | 4.4 | 0.0 | 5.3 |
| EB/Poly's | 7.4 | 12.5 | 18.7 | ∞ | 18.5 |

TABLE III[1],[2]-continued

Alkylation of Benzene with a Dilute Ethylene Stream over Acid Mordenite (SiO$_2$/Al$_2$O$_3$ = 196)

| Run: | A | B | C | D | E |
|---|---|---|---|---|---|
| Ratio | | | | | |

[1]Data of Table II recalculated by subtracting out ethane and benzene feedstreams, hydrogen, and light hydrocarbons
[2]Alkylating feedstream, 12 wt % ethylene with no C3+ compounds.
[3]Ethane GHSV, as delivered to the dehydrogenation reactor.

It is seen that ethane and benzene can be used as feedstocks for the production of ethylbenzene in high selectivity. Under the process conditions illustrated, a gallium-exchanged mordenite is found to be a good catalyst for dehydrogenating ethane to ethylene in high selectivity. Only trace amounts of C3+ hydrocarbons are found in the dehydrogenation stream. Consequently, a dilute stream of ethylene in ethane is obtained which can be used without further purification as an alkylation stream for the alkylation of benzene to ethylbenzene. Xylenes are produced in small amounts only at low alkylation temperatures, and essentially no xylenes are produced at temperatures above 450° C. Moreover, the ethylbenzene to polyethylated benzene weight ratio is very high. This eliminates the need for a transalkylation reactor and reduces losses due to tars and shortened catalyst lifetime.

Example 2

A sample of dry acid mordenite (SiO$_2$/Al$_2$O$_3$=19) is mixed with a 2M solution of zinc nitrate in the ratio 10 ml solution per g of mordenite. The mixture is stirred under reflux for 2 hr. The mixture is cooled and filtered without washing. The full procedure is repeated 3 times. The resulting material is calcined in air at 500° C. overnight and stored as a zinc-exchanged mordenite dehydrogenation catalyst.

The zinc-mordenite is tested in the dehydrogenation microreactor, according to the procedure of Example 1. Process conditions and results are set forth in Table I. It is seen that zinc-impregnated mordenite is capable of dehydrogenating ethane with high selectivity to ethylene and low selectivity to aromatics. The ethylene stream from the dehydrogenation reactor is introduced without further purification to the alkylation microreactor, as in Example 1. Alkylation results are similar to the results shown in Table II.

Example 3

A solution is made by mixing ruthenium (III) chloride (3 moles) with 10 ml of 1M HCl. The solution is mixed with 30 g of dry acid mordenite (SiO$_2$/Al$_2$O$_3$=19). The mixture is mixed until uniform and held overnight. The resulting solid is calcined in air for 3 hr at 500° C. to yield a ruthenium-exchanged mordenite dehydrogenation catalyst.

The Ru-mordenite is tested in the dehydrogenation microreactor, according to the procedure of Example 1. Process conditions and results are set forth in Table I. It is seen that ruthenium-exchanged mordenite is capable of dehydrogenating ethane with high selectivity to ethylene and low selectivity to aromatics. The ethylene stream from the dehydrogenation reactor is introduced without further purification to the alkylation microreactor, as in Example 1. Alkylation results are similar to the results shown in Table II.

Example 4

A sample of dealuminated mordenite is prepared by the method described hereinabove employing calcination and hydrochloric acid treatments, with the exception that the acid-exchanged mordenite is calcined at 700° C. and treated with 6M hydrochloric acid only once and not twice. The dealuminated mordenite has a SiO$_2$/Al$_2$O$_3$ molar ratio of 112. This mordenite is tested in the dehydrogenation microreactor, according to the procedure of Example 1. Process conditions and results are set forth in Table I. It is seen that dealuminated mordenite alone is capable of dehydrogenating ethane with high selectivity to ethylene and low selectivity to aromatics. The ethylene stream from the dehydrogenation reactor is introduced without further purification to the alkylation microreactor, as in Example 1. Alkylation results are similar to the results shown in Table II.

Example 5

The dehydrogenation and alkylation processes of Example 1 are repeated, with the exception that acidic ZSM-5 having a SiO$_2$/Al$_2$O$_3$ molar ratio of 57.4 is employed as the alkylation catalyst rather than acid mordenite. Process conditions and results are shown in Table IV.

TABLE IV

Alkylation of Benzene with a Dilute Ethylene Stream over H-ZSM-5 (SiO$_2$/Al$_2$O$_3$ = 57.4)[1]

| Product Distribution (Wt. %) | Based on all products | | Based on aromatic products | |
|---|---|---|---|---|
| | 450° C. | 550° C. | 450° C. | 550° C. |
| Ethylene Conversion | 87 | 49 | 87 | 49 |
| Selectivities: | | | | |
| Methane | 0.6 | 0.9 | — | — |
| Ethane | 28.5 | 34.2 | — | — |
| Ethylene | 0.6 | 1.9 | — | — |
| Propane | 0.2 | 0.1 | — | — |
| Propylene | 0.3 | 0.8 | — | — |
| Hydrogen | 0.7 | 0.9 | — | — |
| Benzene | 55.3 | 54.9 | — | — |
| Toluene | 1.4 | 2.2 | 10.2 | 34.9 |
| p-Xylene | 0.2 | 0.1 | 1.4 | 1.6 |
| m-Xylene | 0.3 | 0.3 | 2.2 | 4.8 |
| o-Xylene | 0.1 | 0.1 | 0.7 | 1.6 |
| Ethylbenzene (EB) | 10.7 | 3.3 | 78.1 | 52.4 |
| Styrene | 0.3 | 0.1 | 2.2 | 1.6 |
| C9's | 0.0 | 0.2 | 0.0 | 3.2 |
| C10+ Poly's | 0.7 | 0.0 | 5.1 | 0.0 |
| EB/Poly's | — | — | 15.3 | ∞ |

[1]Alkylating feedstream, 12 wt % ethylene with no C3+ compounds. Alkylation run at 1 atm, benzene LHSV = 3.0 hr$^{-1}$, ethane GHSV to the dehydrogenation reactor = 1200 hr$^{-1}$.

What is claimed is:

1. A process of preparing ethylbenzene or substituted ethylbenzene comprising the steps of:
   (A) contacting ethane in a dehydrogenation zone with a catalytic amount of a dehydrogenation catalyst consisting essentially of a mordenite zeolite and, optionally, a promoter metal selected from the group consisting of gallium, zinc, the platinum group metals of the Periodic Table, and combinations thereof, the contacting being conducted under reaction conditions sufficient to provide a dehydrogenation product stream containing predominantly ethylene and unreacted ethane, and
   (B) passing the dehydrogenation product stream with essentially no further purification or separation into an alkylation zone and contacting the dehydrogenation product stream with benzene or substituted benzene in the presence of a catalytic amount of an alkylation catalyst, the contacting being conducted under reaction conditions sufficient to provide ethylbenzene or a substituted ethylbenzene.

2. The process of claim 1 wherein the dehydrogenation catalyst is a mordenite zeolite having a silica to alumina molar ratio between about 10 and about 500.

3. The process of claim 2 wherein the mordenite zeolite is ion-exchanged or impregnated with gallium, zinc, platinum, or ruthenium.

4. The process of claim 1 wherein the dehydrogenation temperature ranges from about 550° C. to about 750° C. and the gas hourly space velocity ranges from about 100 hr$^{-1}$ to about 5,000 hr$^{-1}$.

5. The process of claim 1 wherein the conversion of ethane is greater than about 5 weight percent, and the selectivity to ethylene is greater than about 80 weight percent.

6. The process of claim 1 wherein benzene is employed in the alkylation zone.

7. The process of claim 1 wherein the alkylation catalyst is selected from the group consisting of acid zeolites mordenite, beta, Y and ZSM-5 and porous crystalline magnesium silicates having a composition corresponding to the following formula in terms of the molar ratios of oxides on a dry basis:

$$(M_{2/n}O)_p(MgO)_x(R_2O_3)_y(SiO_2)_z$$

wherein M is at least one cation having a valence of n; R is at least one trivalent element x/z is greater than 0; y/z is greater than or equal to 0; p/n is greater than y; p, x, and z are positive numbers, and y is a positive number or zero.

8. The process of claim 7 wherein the alkylation catalyst is an acidic mordenite zeolite having a SiO$_2$/Al$_2$O$_3$ molar ratio equal to or greater than 30:1, prepared by treating with strong acid an acidic mordenite zeolite having a SiO$_2$/Al$_2$O$_3$ molar ratio of less than 30:1 and a Symmetry Index, as determined by X-ray diffraction, between 0.5 and 1.3, and then calcining the acid treated mordenite, and retreating the calcined mordenite with strong acid.

9. The process of claim 8 wherein the alkylation catalyst is acidic mordenite zeolite having a SiO$_2$/Al$_2$O$_3$ molar ratio of at least about 160:1 and a Symmetry Index of between 1 and 2.

10. The process of claim 1 wherein in the alkylation zone benzene or substituted benzene is in the liquid phase, the product stream from the dehydrogenation zone is dissolved in the liquid phase, and the alkylation temperature ranges from about 100° C. to about 300° C.

11. The process of claim 1 wherein benzene or substituted benzene and the product stream from the dehydrogenation zone are introduced into the alkylation zone in the vapor phase and the alkylation temperature ranges from about 200° C. to about 800° C.

12. The process of claim 1 wherein the alkylation catalyst is acidic zeolite ZSM-5.

13. A process of preparing ethylbenzene comprising the steps of:
  (a) contacting ethane in a dehydrogenation zone with a catalytic amount of a mordenite zeolite, optionally, containing metal ions selected from the group consisting of gallium, zinc, and the platinum group metals, at a temperature between about 550° C. and about 750° C. and a gas hourly space velocity ranging from about 100 hr$^{-1}$ to about 5,000 hr$^{-1}$ so as to form a dehydrogenation product stream containing ethylene and ethane, ethylene being present in a concentration of from about 5 to about 50 weight percent,
  (b) passing the dehydrogenation product stream with essentially no further purification or separation into an alkylation zone, and contacting the dehydrogenation product stream in the alkylation zone with benzene in the presence of an alkylation catalyst, the contacting being conducted in the liquid phase at a temperature between about 100° C. and about 300° C. or in the vapor phase at a temperature between about 200° C. and about 800° C. under reaction conditions sufficient to provide a product stream containing predominantly ethylbenzene and unreacted ethane and benzene.

14. The process of claim 13 wherein the alkylation catalyst is selected from the group consisting of zeolites Y, beta, ZSM-5, and mordenite in the acid forms and porous magnesium silicates having the formula:

$$(M_{2/n}O)_p(MgO)_x(R_2O_3)_y(SiO_2)_z$$

wherein M is at least one cation having a valence of n; R is at least one trivalent element x/z is greater than 0; y/z is greater than or equal to 0; p/n is greater than y; and p, x, z, are positive numbers, and y is a positive number or zero.

15. The process of claim 14 wherein the mordenite has a SiO$_2$/Al$_2$O$_3$ molar ratio greater than or equal to 30, and is prepared by treating with strong acid an acid mordenite having a SiO$_2$/Al$_2$O$_3$ molar ratio less than 30 and having a Symmetry Index, as determined by X-ray diffraction, between 0.5 and 1.3, then calcining the acid-treated mordenite, and retreating the calcined mordenite with strong acid.

16. The process of claim 13 wherein in the dehydrogenation zone the conversion of ethane is greater than about 5 weight percent and the selectivity to ethylene is greater than about 70 weight percent, and wherein in the alkylation zone the conversion of ethylene is greater than about 40 weight percent and the selectivity to ethylbenzene is greater than about 70 weight percent.

17. The process of claim 13 wherein the product stream from the alkylation zone is separated to recover the ethylbenzene product; unreacted ethane is recycled to the dehydrogenation zone; and unreacted benzene is recycled to the alkylation zone.

18. The process of claim 13 wherein ethylbenzene which is formed in the alkylation zone is recycled to the alkylation zone and further alkylated to diethylbenzene.

19. The process of claim 1 wherein the dehydrogenation catalyst consists essentially of mordenite zeolite.

20. The process of claim 1 wherein the dehydrogenation catalyst consists essentially of mordenite zeolite and a promoter metal selected from the group consisting of gallium, zinc, the platinum group metals, and combinations thereof.

* * * * *